US00PP37041P2

(12) United States Plant Patent
Woods

(10) Patent No.: US PP37,041 P2
(45) Date of Patent: Oct. 21, 2025

(54) ***HIBISCUS* PLANT NAMED 'RWOODS7'**

(50) Latin Name: *Hibiscus syriacus*
Varietal Denomination: RWOODS7

(71) Applicant: Roderick Ian Woods, King's Lynn (GB)

(72) Inventor: Roderick Ian Woods, King's Lynn (GB)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 18/964,940

(22) Filed: Dec. 2, 2024

(51) Int. Cl.
*A01H 6/60* (2018.01)
*A01H 5/02* (2018.01)

(52) U.S. Cl.
USPC ..... Plt./257

(58) Field of Classification Search
USPC ..... Plt./257
CPC ..... A01H 6/608; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Hibiscus* plant named 'RWoods7' is disclosed, characterized by pure white flowers with fully overlapping petals. Plants are highly vigorous, with excellent health. The new cultivar is a *Hibiscus*, suitable for ornamental garden purposes.

2 Drawing Sheets

Figure 1:
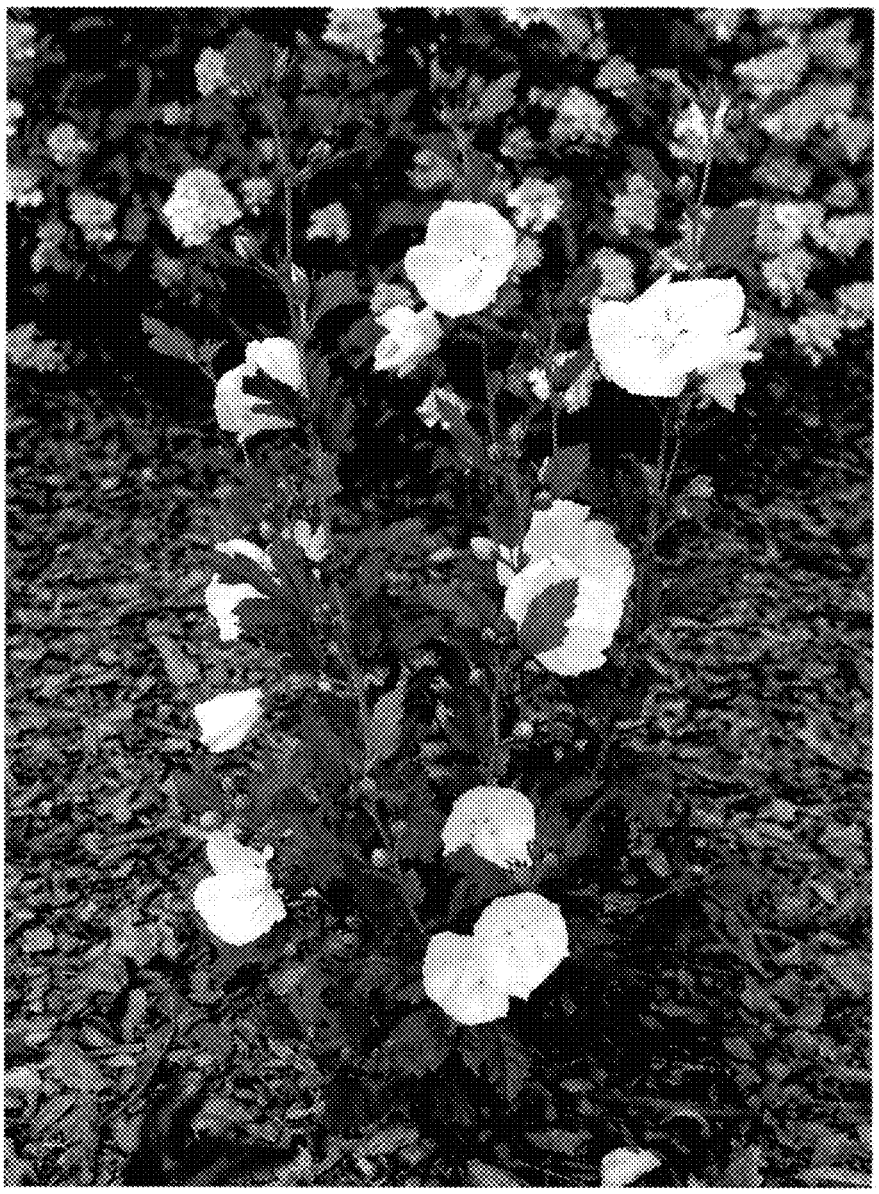

Latin name of the genus and species: *Hibiscus syriacus*.
Variety denomination: 'RWOODS7'.

BACKGROUND OF THE INVENTION

The new cultivar is a product of a planned breeding program by the inventor, to develop sturdy new *Hibiscus* varieties with better flower form and color. The crossing resulting in the new cultivar was made during 2007, at a nursery in Norfolk, United Kingdom. The seed parent is an unpatented internal selection named *Hibiscus* 'Seedling 7650'. The pollen parent is an unpatented internal selection named *Hibiscus* 'Seedling 7077'. The inventor discovered this new cultivar at the same nursery in September 2009.

After identifying the new cultivar as a potentially interesting selection, the inventor first propagated plants of 'RWOODS7' by softwood cuttings in February 2010 at the same nursery in Norfolk, United Kingdom. Multiple generations have been reproduced and have shown that the unique features of this cultivar are stable and reproduced true to type.

SUMMARY OF THE INVENTION

The cultivar 'RWOODS7' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'RWOODS7'. These characteristics in combination distinguish 'RWOODS7' as a new and distinct *Hibiscus* cultivar:

1. Pure white flowers.
2. Wide flower petals that fully overlap, forming a very circular flower up to 14 cm wide.
3. Flower petals which lay very flat, giving the flower a disc-like appearance.

4. Flowers which are durable and resistant to weather such as rain and wind.
5. Highly vigorous/strong growing plant with excellent health.

COMPARISON TO PARENT VARIETIES

'RWOODS7' is similar in most horticultural characteristics to the seed parent cultivar. Plants of the new cultivar 'RWOODS7' however, differ in the following:

1. Flower color of the new cultivar is white, while the flower color of the seed parent is violet-blue with a red eye.

'RWOODS7' is similar in most horticultural characteristics to the pollen parent cultivar. Plants of the new cultivar 'RWOODS7' however, differ in the following:

1. Flower color of the new cultivar is white, while the flower color of the pollen parent is violet-blue with a red eye.

COMMERCIAL COMPARISON

'RWOODS7' can be compared to the commercial cultivar *Hibiscus syriacus* 'Diana', unpatented. Plants of the new cultivar 'RWOODS7' are similar to plants of 'Diana' in most horticultural characteristics, however, plants of the new cultivar 'RWOODS7' differ in the following:

1. Petals of the new cultivar are wide and fully overlapping, while petals of this comparator do not overlap as completely.
2. Petal base of the new cultivar is shorter, resulting in less of a gap at the center. Petal base of this comparator is more elongated, resulting in more of a gap at the center.
3. Petal margins of the new cultivar are more entire, while petal margins of this comparator are more ruffled.

BRIEF DESCRIPTION OF THE PHOTOGRAPHS

The accompanying photograph in FIG. 1 illustrates in full color a flowering plant of 'RWOODS7' grown outdoors in Norfolk, United Kingdom. This plant is approximately 1 year old.

Figure 2:
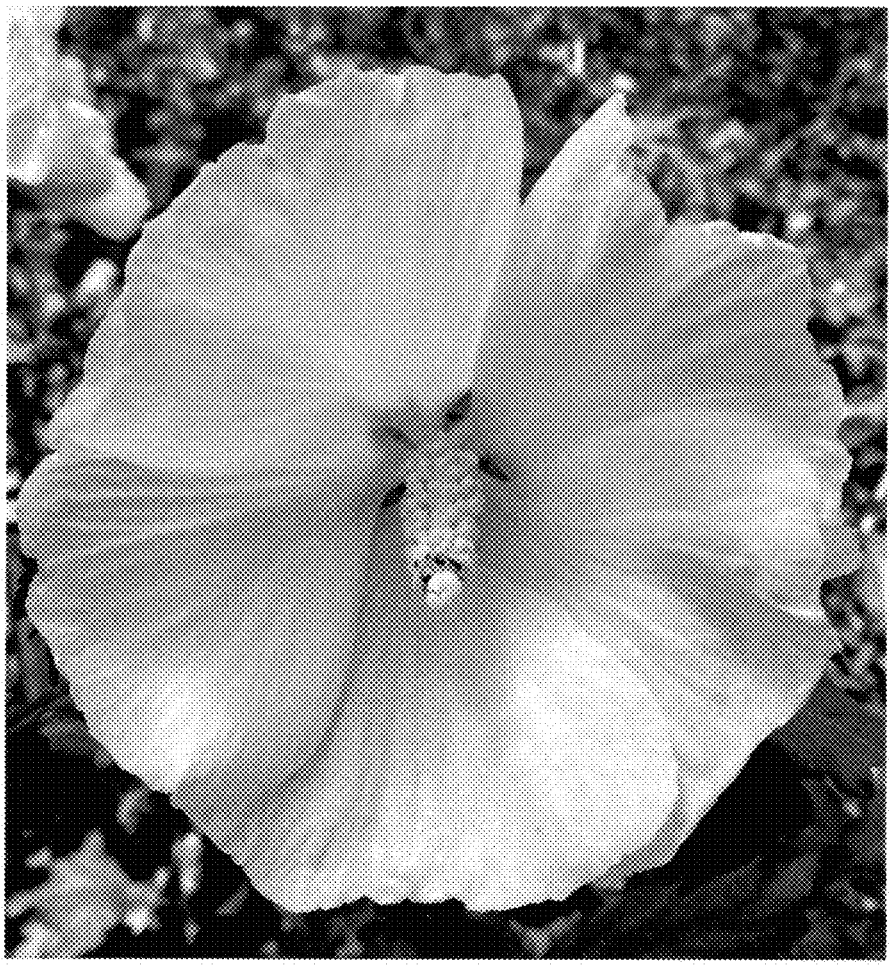

FIG. 2 shows a close-up view of a flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'RWOODS7' plants grown in July of 2024 in a poly-greenhouse in Grand Haven, Michigan. Plants are approximately 3 years old, in 3-gallon containers. The average day time temperature is 18-27° C., average night temperature is 5-10° C. Measurements and numerical values represent averages of typical plant types.

Botanical classification: *Hibiscus syriacus* 'RWOODS7'.

PROPAGATION

Method: Softwood cuttings.
Time to rooting: 25 days in summer.
Time to produce rooted plant: 45 days in summer.
Root description: Dense, freely branching, fleshy, medium thickness. White in color, not accurately measured by the color chart.

PLANT

Plant type: Perennial flowering shrub.
Plant shape: Upright and compact.
Growth habit: Upwards.
Height: 75 cm.
Plant spread: 55 cm.
Growth rate: Moderate.
Plant vigor: Moderately vigorous.
Branching characteristics:
- *Lateral branches*.—Branching Habit: Basal; some pinching required to encourage branching. Quantity: About 15. Length: 60 cm. Diameter: 7 mm.
- *Stem*.—Shape: Rounded. Aspect: 70° to 90°. Strength: Strong. Pubescence: Yes, slight on new growth only. Color: New Growth: RHS Greyed-Green 195A. Old Growth: RHS Grey-Brown 199D.
- *Internode length*.—5 cm.

FOLIAGE

Leaf:
- *Type*.—Single.
- *Arrangement*.—Alternate.
- *Length*.—8 cm.
- *Width*.—4.5 cm.
- *Shape*.—Rhomboidal.
- *Apex*.—Acuminate.
- *Base*.—Cuneate.
- *Margin*.—Dentate, with some leaves exhibiting three distinct lobes.
- *Texture of top surface*.—Coarse and somewhat coriaceous.
- *Texture of bottom surface*.—Coarse and somewhat coriaceous.
- *Pubescence*.—None.
- *Color*.—Young foliage upper side: RHS Green NN137A. Young foliage under side: RHS Yellow-Green 147B. Mature foliage upper side: RHS Green NN137A. Mature foliage under side: RHS Yellow-Green 147B.
- *Venation*.—Pattern: Palmate. Color, upper side: RHS Yellow-Green 146D. Color, under side: RHS Yellow-Green 146D.

Petiole:
- *Length*.—2 cm.
- *Diameter*.—2 mm.
- *Texture, upper side*.—Pubescent.
- *Texture, under side*.—Pubescent.
- *Color, upper side*.—RHS Green 137B.
- *Color, under side*.—RHS Green 137B.

FLOWER

Bloom period: Summer (July-August).
Flowers:
- *Arrangement*.—Flowers borne singly from leaf axils along the lengths of lateral branches, as well as in clusters of 3-5 at the branch apices.
- *Type or form*.—Single, rotate, whorl.
- *Eye zone*.—Absent.
- *Aspect*.—Outward.
- *Quantity of flowers per lateral stem*.—2 to 3.
- *Quantity of buds per lateral stem*.—10 to 15.
- *Quantity of flowers and buds per plant*.—150 to 200.
- *Length*.—12 cm.
- *Diameter*.—12 cm.
- *Depth*.—4 cm.
- *Persistence*.—Self-cleaning.
- *Longevity*.—1 to 2 weeks on plant.
- *Fragrance*.—None.

Bud:
- *Shape*.—Ovate.
- *Length*.—1.5 cm.
- *Diameter*.—1.2 cm.
- *Color*.—RHS Yellow-Green 147B.

Petals:
- *Appearance*.—Silky, pure white petals which overlap completely, leaving no gaps in between.
- *Arrangement*.—Whorl.
- *Length*.—6 cm.
- *Width*.—7.5 cm.
- *Apex*.—Obtuse.
- *Base*.—Cuneate.
- *Shape*.—Reniform.
- *Margin*.—Slightly sinuate.
- *Number*.—5.
- *Fused*.—No.
- *Texture*.—Both sides soft and silky.
- *Color*.—Upper surface at first opening: RHS White NN155B. Under surface at first opening: RHS White NN155B. Upper surface at maturity: RHS White NN155B. Under surface at maturity: RHS White NN155B. Fading, upper side: RHS White NN155B. Fading, under side: RHS White NN155B.

Petaloids:
- *Appearance*.—Small, irregularly shaped.
- *Arrangement*.—Whorl.
- *Length*.—Approximately 2 cm.
- *Width*.—Approximately 3 mm.
- *Apex*.—Rounded.

*Base*.—Attenuate.
*Shape*.—Irregularly oblong.
*Margin*.—Entire.
*Number*.—About 5.
*Fused*.—No.
*Texture*.—Both sides soft and silky.
*Color*.—Upper surface at first opening: RHS White NN155B. Under surface at first opening: RHS White NN155B. Upper surface at maturity: RHS White NN155B. Under surface at maturity: RHS White NN155B.

Sepals:
*Appearance*.—Triangular shaped, fused at base.
*Arrangement*.—Stellate.
*Length*.—2 cm.
*Width*.—1 cm.
*Apex*.—Acute.
*Base*.—Fused.
*Shape*.—Triangular.
*Margin*.—Entire.
*Number*.—About 5.
*Fused*.—No.
*Texture, under side*.—Glabrous.
*Texture, upper side*.—Slightly pubescent with short, coarse hairs.
*Color*.—Upper surface at maturity: RHS Yellow-Green 147B. Under surface at maturity: RHS Yellow-Green 147B.

Calyx:
*Shape*.—Collar-like.
*Length*.—2.5 cm.
*Diameter*.—2.5 cm.

Peduncle:
*Length*.—3 cm.
*Diameter*.—3 mm.
*Color*.—RHS Green 137B.
*Texture*.—Pubescent with short, coarse hairs.
*Aspect*.—45°.
*Strength*.—Strong.

REPRODUCTIVE ORGANS

Stamens:
*Number*.—Around 50, arranged in a staminal column.
*Filament length*.—2 mm.
*Filament color*.—RHS White NN155B.
*Anther shape*.—Globular.
*Anther length*.—2 mm.
*Anther color*.—RHS Greyed-Yellow 162D.
*Pollen amount*.—Moderate.
*Pollen color*.—RHS Greyed-Yellow 162D.

Pistil:
*Number*.—5.
*Length*.—5 mm.
*Style*.—Length: 3 mm. Color: RHS White NN155B.
*Stigma*.—Shape: Peltate; hemispherical. Color: RHS White NN155B.

SEEDS

Seeds:
*Quantity*.—20 to 40 seeds per capusul are borne from dehiscent, five chambered capsules.
*Shape*.—Curved, tear-drop shape, with a filamentous or "hairy" coma around the margin.
*Length*.—5 mm.
*Diameter*.—5 mm.
*Color*.—RHS Brown 200C.

OTHER CHARACTERISTICS

Fruit: Not observed.
Disease and pest resistance: Neither resistance nor susceptibility to normal pests of *Hibiscus* observed.
Temperature tolerance: Tolerant to USDA Zone 5-9.

What is claimed is:

1. A new and distinct cultivar of *Hibiscus* plant named 'RWoods7' as herein illustrated and described.

* * * * *